United States Patent [19]

Auerbach

[11] Patent Number: 5,310,917

[45] Date of Patent: May 10, 1994

[54] PROCESS FOR THE PREPARATION OF 4-SUBSTITUTED-1,4-DIHYDROPYDRINES

[75] Inventor: Joseph Auerbach, Brooklyn, N.Y.

[73] Assignee: Merck & Co., Inc., Rahway, N.J.

[21] Appl. No.: 920,701

[22] Filed: Jul. 28, 1992

Related U.S. Application Data

[63] Continuation-in-part of Ser. No. 759,026, Sep. 13, 1991, abandoned.

[51] Int. Cl.$^5$ ............................................ C07D 211/02
[52] U.S. Cl. ..................................................... 540/249
[58] Field of Search ........................................ 546/249

[56] References Cited

U.S. PATENT DOCUMENTS

| | | | |
|---|---|---|---|
| 4,264,611 | 4/1981 | Berntsson et al. | 424/266 |
| 4,578,395 | 3/1986 | Yamaguchi et al. | 514/356 |
| 4,772,596 | 9/1988 | Koike et al. | 514/210 |

FOREIGN PATENT DOCUMENTS

| | | |
|---|---|---|
| 58993/86 | 12/1986 | Austria . |
| 2040062 | 10/1991 | Canada . |
| 0095451 | 11/1983 | European Pat. Off. . |
| 0212107 | 3/1987 | European Pat. Off. . |
| 0319814 | 6/1989 | European Pat. Off. . |
| 0342182 | 11/1989 | European Pat. Off. . |
| 0370821 | 5/1990 | European Pat. Off. . |
| 0371492 | 6/1990 | European Pat. Off. . |
| 0445987 | 9/1991 | European Pat. Off. . |
| 0451654 | 10/1991 | European Pat. Off. . |

OTHER PUBLICATIONS

U. Eisner and J. Kuthan, *Chem. Rev.*, 72, 1 (1972).
E. Klingsberg, ed. *Pyridine and Its Derivatives:* Part 1, pp. 435–455 (Interscience Publishers, N.Y. 1960).
J. Kuthan and A. Kurfurst, *Ind. Eng. Chem. Prod. Res. Dev.*, 21, pp. 191–261 (1982).
A. Sausins and G. Duburs, *Heterocycles*, 27, pp. 269–289 (1988).
Streitwiser et al., *Introduction to Organic Chemistry*, pp. 272–275, 1097–1098 (MacMillan Publishing, Inc. 1976.).

*Primary Examiner*—Frederick E. Waddell
*Assistant Examiner*—Phyllis G. Spivack
*Attorney, Agent, or Firm*—Catherine A. Dolan; David A. Muthard; Paul D. Matukaitis

[57] ABSTRACT

4-Substituted-1,4-dihydropyridines are prepared by a cycloaddition reaction in which the cyclization is driven to completion, after thermal reaction, by addition of an acid. Felodipine, a vasodilator, is prepared by a cycloaddition reaction of ethyl 3-aminocrotonate with a suitably substituted dichlorobenzylidine under reaction conditions whereby the product crystallizes out of the reaction solution and may be directly isolated by filtration.

24 Claims, No Drawings

PROCESS FOR THE PREPARATION OF 4-SUBSTITUTED-1,4-DIHYDROPYDRINES

RELATED APPLICATION

The present application is a continuation-in-part of copending application Ser. No. 759,026, filed Sep. 13, 1991, now abandoned.

BACKGROUND OF THE INVENTION

Felodipine, the compound of Formula Ib, is a known vasodilator (Merck Index 11,3895 and references cited therein). Other phenyl-1,4-dihydro- pyridine compounds have also been disclosed which have therapeutic activity in the treatment of heart disease (see for example: U.S. Pat. Nos. 4,220,649; 4,705,797; 4,769,374; 4,806,544; 4,874,773; and EPO Appl. Nos. 0 089 167, 0 063 365 and 0 342 182).

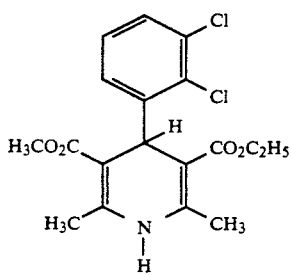

Ib

The preparation of felodipine and related compounds typically involves a multistep synthesis, the last step of which usually involves formation of the dihydropyridine ring. Formation of the 4-aryl dihydropyridines has been accomplished by either simultaneous reaction of an aromatic aldehyde, an acetoacetate ester and a 3-aminocrotonic acid ester in an alcohol solvent (see for example U.S. Pat. No. 4,264,611) or a stepwise procedure of reacting an aromatic aldehyde with an acetoacetate ester and then reacting the resulting benzylidene with a 3-amino crotonic acid ester (see for example: EPO Appl. No. 0 319 814). Regardless of whether the sequence of reactions is a single step or two steps, the disclosed cycloadditions have always been thermally driven to completion. Thermal cycloaddition reactions have also been described which are carried out in the presence of an organic base or the acetic acid salt of an organic base (see for example U.S. Pat. No. 4,772,596 and EP-0 370 974). The two procedures are illustrated below.

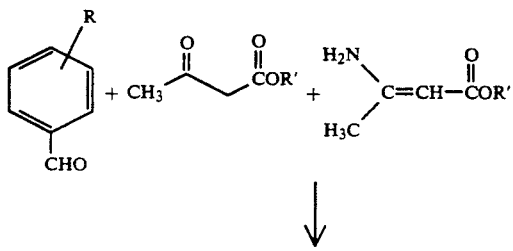

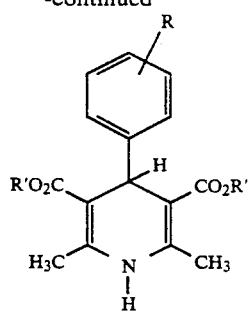

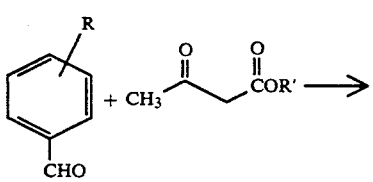

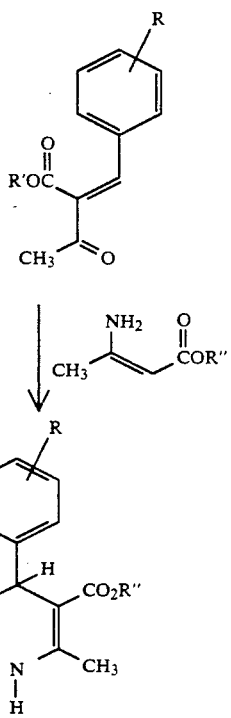

EP - 0371492 discloses that when the latter reaction (R''=2-haloethyl) is carried out in the presence of a dehydrating agent such as molecular sieves, the desired aryldihydropyridine product is obtained in improved yields and with fewer by-products.

Other analogous processes for the preparation of felodipine are known in the art (see for example: Span. Appl. Nos. ES-536,229; 537,424; and 549,753).

In most of the disclosed syntheses of aryldihydropyridine diesters isolation of the product from the reaction mixture required an extractive workup that typically employed a halogenated solvent. Also because a low-molecular-weight alcohol is typically employed as a solvent in the cycloaddition reaction, such an extractive workup of the crude reaction requires that the solvent first be distilled away.

It is an object of the instant invention to provide a process, for the preparation of 4-substituted-1,4-dihydropyridines having shorter thermal reaction times, and, as a consequence, having lower weight percentages of undesirable impurities, than processes previously known in the art.

It has been surprisingly discovered that, under optimal reaction conditions designed to minimize the formation of impurities, the ring closure in the cycloaddition reaction of substituted 3-aminocrotonate and substituted benzylidine is not thermally driven to completion; rather, a strong acid can be added to the reaction mixture subsequent to the foreshortened heating period to catalyze and facilitate the complete cyclization to provide the 4-substituted-1,4-dihydropyridine.

It is also an object of the instant invention to provide an improved process for the preparation of felodipine having higher yields than processes previously known in the art.

It is further an object of the instant invention to provide a process for the preparation of felodipine wherein the crude felodipine is isolated by filtration of the reaction mixture, thereby eliminating the need for a more expensive and time-consuming extractive isolation procedure, which might employ environmentally harmful halogenated solvents.

SUMMARY OF INVENTION

The present invention provides a novel process for the preparation of a compound having the formula I:

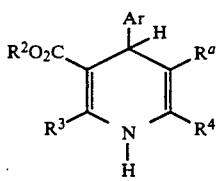

wherein
Ar is selected from:

a) 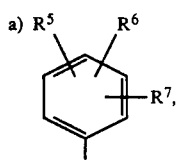

b) 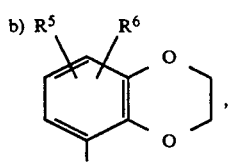

c) 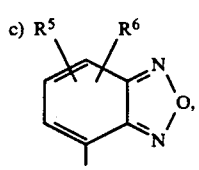

d) 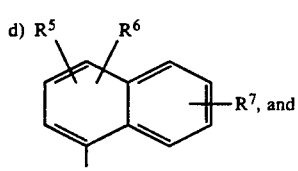

e) 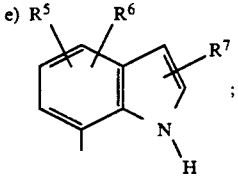

$R^a$ is selected from:

a) $\underset{COR^1}{\overset{O}{\|}}$, b) $\underset{CNR^8R^9}{\overset{X}{\|}}$, and c) CN;

$R^1$ and $R^2$ are independently selected from:
a) $C_1$–$C_8$-alkyl,
b) $C_3$–$C_8$-cycloalkyl,
c) $C_2$–$C_5$-alkenyl,
d) $C_1$–$C_4$-aralkyl,
e) $C_2$–$C_4$-aralkenyl
f) –$C_1$–$C_5$-alkylNR$^8$R$^9$,
g) –$C_1$–$C_4$-alkyl-O-$C_1$–$C_4$-alkyl,
h) –$C_1$–$C_4$-alkylONO$_2$, i) 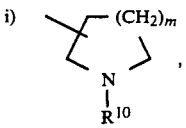

j) 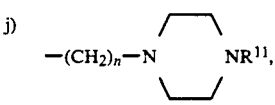

k) 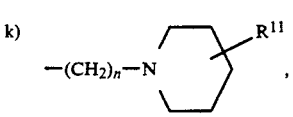

l) 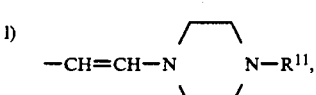

m) 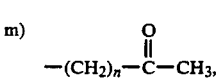

n) 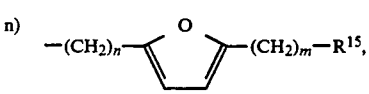

o) 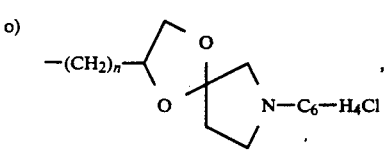

p) 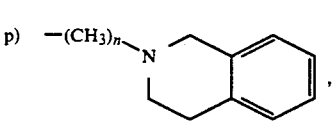

q) 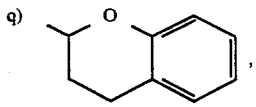

r) 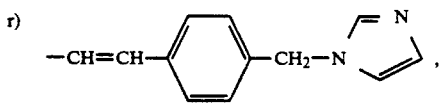

s) 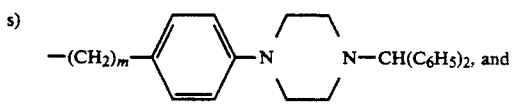

t) 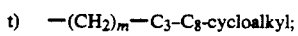

wherein $C_1$-$C_4$ aralkyl is selected from $C_1$-$C_4$ alkyl substituted one to two times with a group selected from: phenyl and naphthyl;

wherein $C_2$-$C_4$ aralkenyl is selected from $C_2$-$C_4$ alkenyl substituted one to two times with a group selected from: phenyl and naphthyl;

$R^3$ is selected from:
a) $C_1$-$C_8$-alkyl,
b) $C_3$-$C_8$-cycloalkyl,
c) $(CH_2)_n$—$R^{12}$, and
d) hydrogen;

$R^4$ is selected from:
a) $C_1$-$C_8$-alkyl,
b) $C_3$-$C_8$-cycloalkyl,
c) $(CH_2)_n$—$R^{12}$, and
d) hydrogen;

$R^5$, $R^6$, and $R^7$ are independently selected from:
a) hydrogen,
b) halogen,
c) $NO_2$, d) 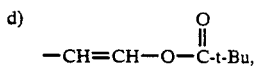

e) $CF_3$,
f) $C_1$-$C_8$-alkyl,
g) $C_3$-$C_8$-cycloalkyl,
h) ethynyl,
i) —$(CH_2)_n$—$R^{12}$, j) 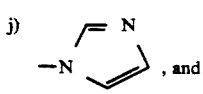

k) 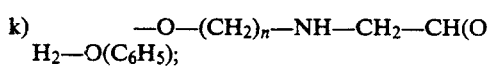

$R^8$ and $R^9$ are independently selected from:
a) $C_1$-$C_8$-alkyl,
b) $C_3$-$C_8$-cycloalkyl,
c) $C_1$-$C_4$-aralkyl as defined herein above, and
d) hydrogen;

$R_{10}$ is selected from:
a) hydrogen,
b) $C_1$-$C_8$-alkyl,
c) $C_3$-$C_8$-cycloalkyl, and
d) $C_1$-$C_4$-aralkyl;

$R^{11}$ is selected from:
a) hydrogen,
b) $C_1$-$C_4$-aralkyl,
c) dichlorophenyl,
d) $C_1$-$C_8$-alkyl, and
e) $C_3$-$C_8$-cycloalkyl;

$R^{12}$ is selected from:
a) halogen,
b) $NR^8R^9$,
c) $NHC(O)$-$C_1$-$C_8$-alkyl;
d) $SR^8$,
e) $SO_2$-pyridyl,
f) $OR^8$, and
g) $CO_2R^8$;

$R^{15}$ is selected from:
a) —$NR^8R^9$, and
b) -1-piperidnyl;

X is O, S or $NR^8$;
m is 0 to 2; and
n is 0 to 3;

comprising the steps of:
heating a mixture of a benzylidine of the formula II:

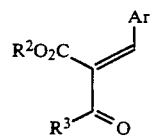

wherein Ar, $R^2$, and $R^3$ are as defined hereinabove and a compound of the formula III:

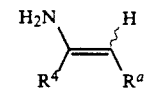

wherein $R^a$ and $R^4$ are as defined hereinabove, in a solvent at an elevated temperature and for a length of time, with a strong acid, wherein the strong acid is added prior to heating to the elevated temperature or subsequent to heating to the elevated temperature, to form the compound of the formula I.

The term "$C_1$-$C_8$-alkyl" includes straight and branched chain alkyl groups having from 1 to 8 carbons. The term $C_1$-$C_8$-alkyl includes methyl, ethyl, isopropyl, propyl, butyl, sec-butyl, t-butyl, n-pentyl, and the like.

The term "$C_3$-$C_8$-cycloalky" includes cyclic alkyl groups having from 3 to 8 carbons. The term $C_3$-$C_8$-cycloalkyl includes cyclopropyl, cyclobutyl, and the like.

The term "$C_2$-$C_5$-alkeny" includes straight and branched chain carbons groups having from 2 to 5 carbon atoms and having one -unsaturated bond. The term includes vinyl, allyl, 2-butenyl and the like.

The term "solvent" includes water miscible solvents and water immiscible solvents. The preferred solvent is a water miscible solvent.

The term "water miscible solvents" include low-molecular-weight alcohols, acetonitrile, dimethylformamide (DMF), tetrahydrofuran (THF), dioxane, methoxyethanol, tetramethylene sulfone, dimethoxyethane and the like. The preferred water miscible solvent is a low-molecular-weight alcohol.

The term "water immiscible solvent" includes benzene, toluene, xylenes, chlorobenzene, o-dichlorobenzene, chloroform, methylene chloride, 2,2,4-trimethylpentane, Dowtherm, and the like.

The term "low-molecular-weight alcohol" includes hydroxy alkane compounds having from 1 to 4 carbon atoms and includes branched and straight chain and cyclic alcohols. The term includes methanol, ethanol, iso-propanol, butanol, isobutanol, cyclohexanol and the like.

The term "halogen" includes chlorine, fluorine, bromine, and iodine.

The term "elevated temperature" represents an temperature sufficiently high to maintain conversion of the starting materials but also sufficiently low to avoid decomposition of the starting materials, intermediates and the product of the formula I. The term includes temperatures between 35° C. and 285° C. A preferred temperature is between 65° C. and 130° C.

The term "length of time" represents a period of time sufficiently long to consume the maximum amount of the starting materials but sufficiently short to allow only a minimum amount of the starting materials, intermediates or product to decompose. The term includes times of 5 minutes to 10 hours. A preferred length of time is a time length between 30 mins and 2 hours.

The term "strong acid" includes aqueous acid solutions, non-aqueous acid solutions and gaseous acids.

The term "aqueous acid solution" includes aqueous mineral acids, optionally with a low-molecular-weight alcohol co-solvent.

The term "non-aqueous acid solution" includes solutions of acids in a water miscible solvent, concentrated sulfuric acid, methane sulfonic acid, trifluoromethane sulfonic acid, nitric acid, chloroacetic acid, dichloroacetic acid, trichloroacetic acid, fluoroacetic acid, difluoroacetic acid, trifluoroacetic acid, chlorosulfonic acid, amberlite sulfonic acid resin and the like. The term also includes solutions of Lewis acids, such as aluminum chloride and the like, and the hydrolytic products of addition of a Lewis acid to a aqueous or protic medium.

The term gaseous acids include hydrogen chloride gas, hydrogen bromide gas, hydrogen fluoride gas and the like.

The term "aqueous mineral acid" includes aqueous hydrogen chloride, aqueous hydrogen bromide, aqueous hydrogen iodide, aqueous phosphoric acid, aqueous perchloric acid and the like. A preferred aqueous mineral acid is aqueous hydrogen chloride.

It is understood that if any functional group substituent, which is part of the starting materials or product of the process disclosed in the instant invention, is incompatible with the chemical transformations of the instant invention (i.e., a particular carboxylic ester may be particularly labile in an acidic solution) a person of ordinary skill in the art would not choose a starting material containing such a group. Alternatively, the incompatible group may be selectively protected, by techniques known in the art, prior to employing a starting material in the process of the instant invention; and subsequent to isolation of such a "protected" product of the instant process, the protection may be removed from the substituent by techniques well known in the art.

It is intended that the definition of any substituent (e.g., $R^8$, $R^9$, $R^{12}$, etc.), which may occur more than once in a particular compound, is independent of its separate occurances. Thus, in a given compound, $R^3$ may be —$CH_2R^{12}$ where $R^{12}$ is $OCH_3$ and $R^4$ may be —$CH_2R^{12}$ where $R^{12}$ is chlorine.

One embodiment of the process of the instant invention is that process wherein the strong acid is added subsequent to an initial period of heating the reaction solution in the absence of the strong acid.

In a class of this embodiment of the process of the instant invention is that process wherein the low-molecular-weight alcohol is ethanol or isopropanol.

In a subclass of this embodiment is the process wherein the solution of aqueous hydrochloric acid in a low-molecular-weight alcohol is 6N aqueous HCl in ethanol.

In another class of this embodiment of the instant invention is the process wherein the internal reaction temperature is 84° C.

In another embodiment of the present invention is the process for the preparation of a compound having the formula Ia:

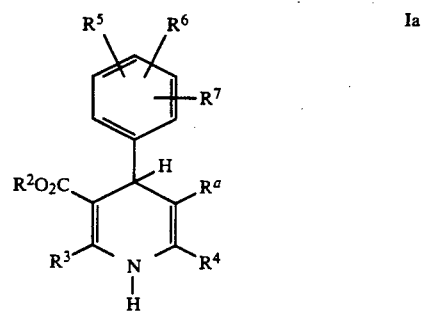

wherein
$R^a$ is selected from:

a) $\underset{COR^1}{\overset{O}{\|}}$, b) $\underset{CNR^8R^9}{\overset{X}{\|}}$, and c) CN;

$R^1$ and $R^2$ are independently selected from:
a) $C_1$-$C_8$-alkyl,
b) $C_3$-$C_8$-cycloalkyl,
c) $C_2$-$C_5$-alkenyl,
d) $C_1$-$C_4$-aralkyl,
e) $C_2$-$C_4$-aralkenyl,
f) -$C_1$-$C_4$-alkyl-O-$C_1$-$C_4$-alkyl,
g) -$C_1$-$C_4$-alkyl-$ONO_2$, h) $-(CH_2)_n-\overset{O}{\overset{\|}{C}} CH_3$, and i) 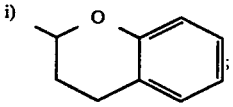;

$R^3$ is selected from:
a) $CH_3$,
b) $CH_2F$,
c) CN, and
d) $CH_2$—$SO_2$—pyridyl;
$R^4$ is selected from:
a) $CH_3$,
b) $(CH_2)$—$NR^8R^9$, and
c) $(CH_2)_n$—$OR^{12}$;
$R^5$, $R^6$, and $R^7$ are independently selected from:

a) hydrogen,
b) halogen,
c) $NO_2$, d) $-CH=CH-O-\overset{O}{\underset{\|}{C}}-t\text{-Bu}$, e) $C_1$-$C_8$-alkyl, and
f) $-O-(CH_2)_n-NH-CH_2CH(OH)CH_2O(C_6H_5)$;

$R^8$ and $R^9$ are independently selected from:
a) $C_1$-$C_8$-alkyl,
b) $C_3$-$C_8$-cycloalkyl,
c) $C_1$-$C_4$-aralkyl, and
d) hydrogen;

$R^{10}$ is selected from:
a) hydrogen,
b) methyl, and
c) $C_1$-$C_4$-aralkyl;

$R^{11}$ is selected from:
a) hydrogen,
b) $C_1$-$C_4$-aralkyl, and
c) dichlorophenyl;

$R^{13}$ is selected from:
a) $-C(O)NH_2$, and
b) $(CH_2)_n-NHCH_2C(O)NH_2$;

$R^{14}$ is hydrogen;
m is 0 to 2; and
n is 0 to 3;
comprising the steps of:
heating a mixture of a benzylidine of the formula IIa:

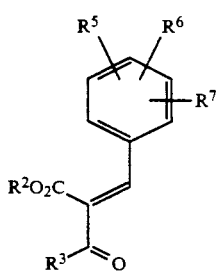

wherein $R^2$, $R^3$, $R^5$, $R^6$ and $R^7$ are as defined hereinabove and a compound of the formula III:

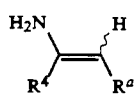

wherein $R^a$ and $R^4$ are as defined hereinabove, in a solvent which is a water miscible solvent at an elevated temperature and for a length of time between 5 minutes and 10 hours;

THEN TREATING the reaction mixture with an aqueous acid solution to provide the compound of the formula Ia.

A class of this embodiment of the present invention is the process for the preparation of felodipine, having the formula Ib:

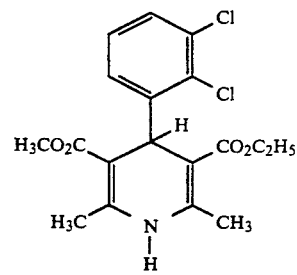

COMPRISING THE STEPS of heating a mixture of a dichlorobenzylidine of the formula IIb:

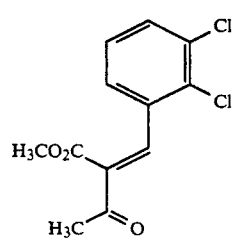

and ethyl 3-aminocrotonate in a low-molecular-weight alcohol at an elevated temperature and for a length of time between 30 minutes and 6 hours; and ADDING a strong acid to the reaction mixture; to provide felodipine.

A subclass of this class of the present invention is the process which further comprises the steps of:

COOLING the solution to cause crystallization, AND collecting the crude felodipine by filtration.

In a subclass of this class of the instant invention is the process wherein the strong acid is a 1:1 v/v mixture of 6N aqueous HCl and ethanol.

In another subclass of this class of the instant invention is the process wherein the strong acid is selected from a 1:1 v/v mixture of 6N aqueous HCl and isopropanol; concentrated (37%) aqueous HCl or anhydrous methane sulfonic acid.

In another subclass of this class of the instant invention is the process which further comprises the step of heating the reaction mixture containing the strong acid for an additional length of time at an elevated temperature.

In another subclass of this class of the instant invention is the process wherein ethyl 3-aminocrotinate is used in molar excess to the dichlorobenzylidine of the formula IIb and the molar amount of strong acid added to the reaction mixture is equal to approximately the molar excess of ethyl 3-aminocrotonate employed.

DETAILED DESCRIPTION OF THE INVENTION

The following synthetic Scheme 1 illustrates a reaction sequence in which the process of the instant invention is employed. It is understood that this scheme is meant to be illustrative and is not limiting. The substituents Ar, $R^a$, $R^2$, $R^3$, and $R^4$ are as defined hereinabove.

Scheme 1

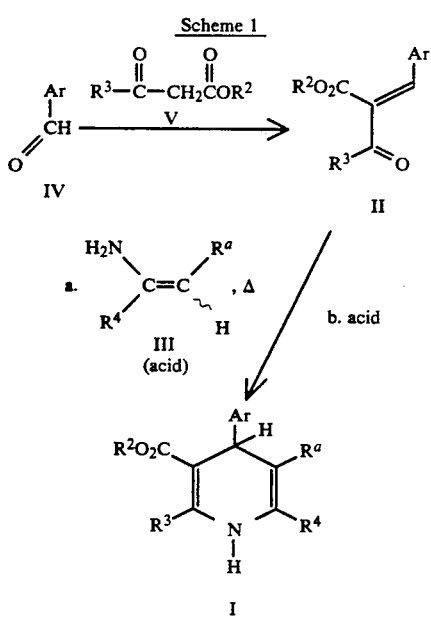

The starting compounds (compounds III, IV and V) employed in the synthetic scheme are known in the art and are readily available either commercially or by following the procedures described in the literature. For example, syntheses of such starting compounds are described in the following patents and publications: U.S. Pat. Nos. 4,220,649; 4,264,611; 4,705,797; 4,769,374; 4,772,596, 4,806,544; 4,874,773; EPO Application Nos. 0 089 167, 0 095 451, 0 063 365, 0 257 616, 0 319 814, 0 342 182, 0 370 821, 0 370 974, 0 371 492, and S. M. Jain et al., *Indian J. Chem.*, 29B, 95 (1990).

In words relative to the equations, the suitably substituted benzaldehyde, VI, such as 3-nitrobenzaldehyde, 2-nitrobenzaldehyde, 2,3-dichlorobenzaldehyde and the like, is reacted with a suitably substituted β-keto acid ester V, such as ethyl acetoacetate, methyl acetoacetate, cyclopropyl acetoacetate and the like, in the presence of a suitable catalyst, such as acetic acid, piperidine, a mixture of acetic acid and piperdine and the like, to provide the benzylidine II. The benzylidine II is reacted with a suitably substituted enamine III, such as ethyl 3-aminocrotonate, 3-aminocrotonic proparygylamide and the like, in a suitable low-molecular-weight alcohol solvent, such as methanol, ethanol, isopropanol and the like, and optionally in the presence of a strong acid, and the mixture was heated at reflux for 10 minutes to 10 hours. The molar ratios of compound II to compound III employed in the the reaction is in the range between 0.66 and 1.5. It is preferred that the strong acid is not present while the mixture is heated for the initial period of time. Preferably, heating is continued until the limiting reagent (whichever of compound II and compound III is not in excess) is consumed. If strong acid is not initially present in the reaction mixture, the heating source may be removed, and the mixture may be cooled slightly, and a strong acid, such as aqueous hydrogen chloride solution, aqueous sulfuric acid solution, anhydrous methane sulfonic acid, and the like, which may contain additional co-solvents, such as water, ethanol, isopropanol, dimethoxyethane and the like or mixtures thereof, is added slowly. The reaction product may then be recovered by extractive workup with a suitable organic solvent, such as methylene chloride, ethyl acetate and the like, or may be isolated, where possible, by cooling and, optionally seeding, the crude reaction mixture, thereby inducing crystallization of the neutral compound or its acid salt when that species is formed, and by subsequently collecting the product by filtration.

Alternatively, if the strong acid is not initially present a strong acid as described above may be added after the initial heating period and the reaction may be heated for an additional time, such as a period selected from 10 minutes to 2 hours. The reaction mixture may then be cooled and the reaction product may be recovered as described above by extractive workup or by cooling-/seeding/filtration.

The following Scheme 2 illustrates a reaction sequence in which the process of the instant invention is employed in the synthesis of felodipine. It is understood that this scheme is meant to be illustrative and is not limiting.

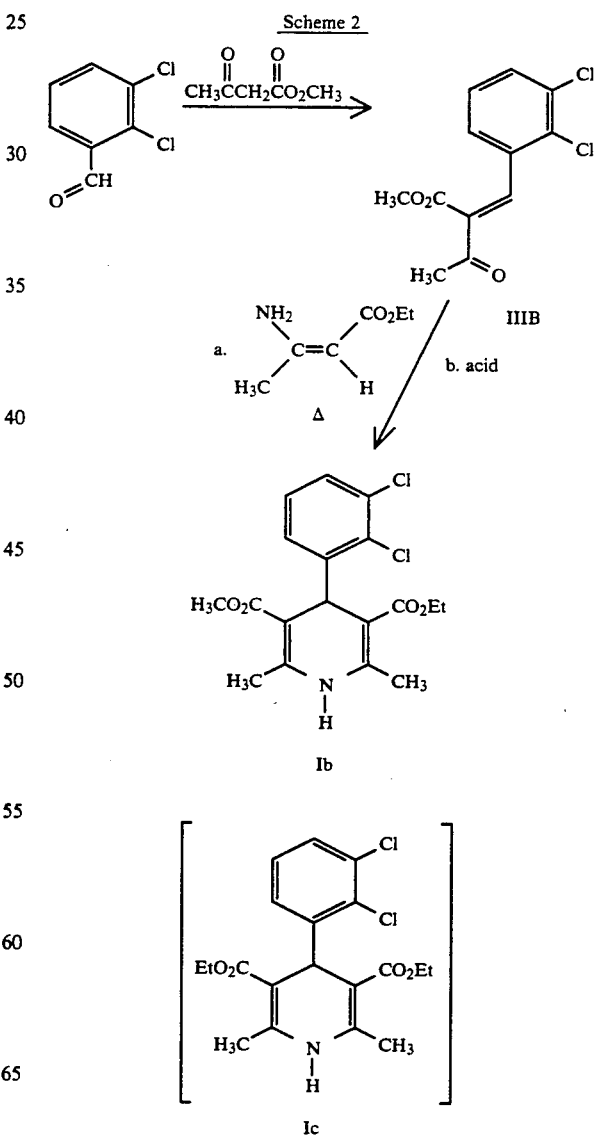

-continued
Scheme 2

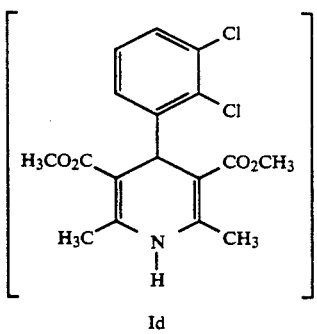

Id

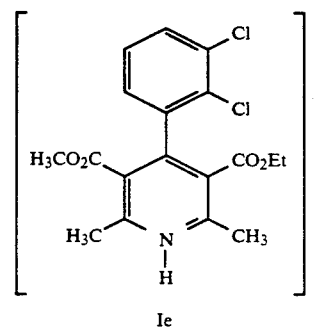

Ie

The reagents employed in the synthetic scheme are well known in the art and are all readily commercially available.

In words relative to the equations, 2,3-dichlorobenzaldehyde is reacted with methyl acetoacetate, in the presence of a suitable catalyst, such as piperidine, acetic acid, a mixture of piperidine and acetic acid, and the like, to provide after aqueous workup the dichlorobenzylidine IIa. A mixture of the benzylidine IIa and ethyl 3-aminocrotonate in a suitable low-molecular-weight alcohol solvent, such as methanol, ethanol, isopropanol, and the like, is heated at reflux for a suitable period of time, such as a time between 30 minutes and 20 hours. The concentration of the reactants in the solvent may be selected from a range of 0.5 remoles of the dichlorobenzylidine IIa/mL of solvent to 5 remoles of IIa/mL of solvent. Preferred is a concentration of 1.0 mmole of IIa/mL of solvent. The mixture may then be cooled slightly and a solution of aqueous HCl and a suitable low-molecular-weight solvent, such as 6N aqueous HCl and ethanol and the like, is added dropwise to the mixture. The mixture is then further cooled, the product thereby crystallizing out of solution and the product was then collected by filtration, rinsed with appropriate solvents, such as cold aqueous ethanol solutions and the like, and dried under vacuum. The crude product may contain small quantities of compounds of Formulas Ic, Id and Ie as minor impurities. The crude product Ia thus obtained can subsequently be recrystallized from an appropriate solvent, such as an isopropanol/water mixture and the like.

Alternatively, if the strong acid is not initially present, a strong acid as described above may be added after the initial heating period and the reaction may be heated for an additional time, such as a period selected from 10 minutes to 2 hours. The reaction mixture may then be cooled and the reaction product may be recovered as described above by extractive workup or by cooling/seeding/filtration. A particular method of direct isolation by crystallization and filtration comprises the addition of water or another solvent such as methyl-t-butylether and the like, to the reaction mixture after the additional heating period.

The invention is further defined by reference to the following examples, which are intended to be illustrative and not limiting. For instance, it is understood that the following known vasodialators/calcium channel blockers may be prepared by reactions similar to the reactions set out in the examples: amlopine, cronidipine, diperdipine, furaldipine, lacidipine, manidipine, mepirodipine, nicardipine, nifedipine, nilvadipine, nimodipine, nisoldipine, nitrendipine, sagandipine and taludipine.

In the Examples all temperatures are in degrees Celsius. All purity percentages disclosed were determined by HPLC (reverse phase C-18 column; MEOH/CH$_3$CN/phosphate at pH$_3$ elution; detector at 254 nm) and yields given are based on pure felodipine. Pot temperatures represent actual temperature of the reaction solution as determined by an in situ digital thermometer.

EXAMPLE 1

Preparation of Felodipine Involving Shortened Thermal Period and Subsequent Acid Catalysis with 12N HCl Solution A stirred mixture of 81 gm of dichlorobenzylidine IIb (98.23% pure by HPLC, 291.34 mmol) and ethyl-3-aminocrotonate 46.67 gm (99.2% by GC, 358.3 mmol) in 75 mL of ethanol (anhydrous) under an argon atmosphere was heated to reflux rapidly and maintained at reflux (84° C. pot temp.) for 1 hour. The heating mantle was removed and the stirred reaction mixture cooled in air to a pot temperature of 75° C. An ethanolic aqueous hydrochloric acid solution (22.5 mL of 12.1N HCl+22.5 mL of water+45 mL of ethanol, mixed and brought to room temperature) was added to the hot solution over 5 minutes time. The reaction mixture was allowed to cool to 41° C. and crystallization began. The mixture was then sequentially cooled to room temperature; cooled in an ice bath and then refrigerated over the weekend. The solids were filtered cold and washed in portions with 300 mL of 1/1 v/v ethanol/water solution at −10° to −15° C. The pH of the filtrate at the end of washing was about pH 5. The solid was suction dried under a nitrogen stream then dried under high vacuum at 40° C. overnight to provide 94.3 gm of product (HPLC 98.9% pure) 83.3% yield. Diethyl ester impurity 0.33 wt. % by HPLC.

EXAMPLE 2

Preparation of Felodipine Involving Shortened Thermal Period and Subsequent Acid Catalysis with 1N HCl Solution A stirred mixture of 27 g. of dichlorobenzylidine IIb (99.7% pure by HPLC, 98.6 mmol) and 15.7 g. of ethyl 3-aminocrotonate (121.3 mmol) in 25 mL of anhydrous ethanol under an argon atmosphere was rapidly heated to 83° C. (reflux) and the solution maintained at reflux for 1.5 hours. The heating mantle was then removed and the solution temperature was allowed to fall to 75° C. A solution of 15 mL 1N aqueous HCl and 15 mL ethanol was added dropwise over a 5 min. period to the hot solution. At the end of the acid addition the temperature was 48° C. The solution was allowed to continue cooling and crystallization began at 33° C. The reaction mixture was allowed to cool to 25° C., then it was cooled in an ice bath for 45 minutes and then refrigerated over the weekend. The solids were filtered cold and washed with 1:1 v/v ethanol/H₂O (precooled to −20° to −25° C). The pH of the filtrate at the end of the washing was about pH 7. The solid was suction dried under a nitrogen stream then dried under high vacuum at 40° C. overnight to provide 30.6g. of the desired product (HPLC 80.3% pure) 64.8% yield.

EXAMPLE 3

Preparation of Felodipine Involving Shortened Thermal Period and Subsequent Acid Catalysis with 12.1N HCl Solution Followed by Further Heating of the Reaction A stirred solution of dichlorobenzylindine IIb (27.0 g., 98.86 mmol) and ethyl-3-aminocrotinate (15.77 g.) in 100 mL of anhydrous ethanol was heated over 23 minutes to 81° C. under argon atmosphere. The reaction mixture was maintained at 80°-81° C. for 1.5 hours and then 2 mL of concentrated aqueous HCl (24.2 mmol) was added rapidly to the reaction mixture. The reaction mixture was maintained at 80°-81° C. for an additional 0.5 hour. A-t the end of this time 50 mL of water was added to the reaction mixture over 10 minutes while the internal temperature of the solution was maintained at 70°-75° C. The reaction solution was cooled to 66° C. and seeded with pure felodipine. The mixture was then allowed to cool linearly over 8 hours to 0° C. The solid which formed was filtered off cold and washed with 100 mL of 1/1 EtOH/H₂O at −10° C. The solid was then dried under vacuum at 45°-50° C. to provide 33.3 g. of felodipine (87.65% yield, 99.6 area % pure). The solid contained 0.13 area % of the diethyldihydro- pyridine Ic. An additional 1.14% yield of felodipine was present in the original filtrate.

EXAMPLE 4

Preparation of Felodipine Involving Shortened Thermal Period and Subsequent Acid Catalysis with Methane Sulfonic Acid Followed by Further Heating of the Reaction A stirred solution of dichlorobenzylindine IIb (27.0 g., 98.86 mmol) and ethyl-3-aminocrotinate (15.77 g.) in 125 mL of anhydrous ethanol was heated over 25 minutes to 81° C. under argon atmosphere. The reaction mixture was maintained at 80°-81° C. for 1.5 hours and then 2.34 g of anhydrous methane sulfonic acid (24.2 mmol) was added rapidly to the reaction mixture. The reaction mixture was maintained at 80°-81° C. for an additional 1.0 hour. At the end of this time 62.5 mL of water was added to the reaction mixture over 10 minutes while the internal temperature of the solution was maintained at 70°-75° C. The reaction solution was cooled to 66° C. and seeded with pure felodipine. The mixture was then allowed to cool linearly over 8 hours to 0° C. The solid which formed was filtered off cold and washed with 100 mL of 1/1 EtOH/H₂O at −10° C. The solid was then dried under vacuum at 45°-50° C. to provide 31.6 g. of felodipine (82.69% yield, 98.4 area % pure). The solid contained 0.28 area % of the diethyldihydropyridine Ic and 0.21 area % of the dimethyldihydropyridine Id. An additional 17% yield of felodipine was present in the original filtrate.

EXAMPLE 5

Preparation of Felodipine Involving Shortened Thermal Period Without Subsequent Acid Catalysis A stirred solution of 27 g. of dichlorobenzylidine IIb (99-100% pure, 99 mmol) and 15.9 g (122.7 mmol) of ethyl 3-aminocrotonate in 25 mL of anhydrous ethanol under an argon atmosphere was rapidly heated to 87° C. (reflux) and the solution maintained at reflux for 1.5 hours. The heating mantle was then removed and the solution temperature was allowed to cool to room temperature (30 mins.). Crystallization was observed when the solution temperature reached 60° C. The mixture was then cooled in an ice bath for 30 mins. and then refrigerated over the weekend. The mixture was again cooled in an ice bath and a 1:1 v/v ethanol:water solution (30 mL) was added dropwise. The mixture was then stirred 1 hour in the ice bath, then filtered and the solid washed with 90 mL of ethanol/water (precooled). The solid was suction dried under a nitrogen stream, then dried under high vacuum at 40° C. overnight to provide 27.5 g of the desired product I (HPLC:61.7% pure) 44.5% yield.

EXAMPLE 6

Preparation of Felodipine Involving Concurrent Acid Catalysis/Thermal Cyclization A mixture of 27 grams of dichlorobenzylidine IIb (98.9 mmol) and 15.8 grams of ethyl 3-aminocrotonate (1.23 equivalents) was suspended in 25 mL of ethanol. To the stirred slurry was added at room temperature a solution of 7.5 mL of concentrated HCl mixed with 7.5 mL of water and 15 ml of ethanol. The mixture was heated to a pot temperature of 84° C. over 10 minutes and maintained there for 2 hours. The mixture was then cooled to 26° C. and seeded with felodipine. The mixture was stirred at ice bath temperature for 0.5 hour and kept overnight at 0° to 6° C. The reaction solids were filtered off and washed with ice cold 50% v/v ethanol/water (−10° to −15° C.) then suction dried at room temperature. The solids were then dried under high vacuum overnight to provide 5.1 grams of a yellowish-white solid (A). The mother liquors from the filtration were neutralized with sodium bicarbonate and then extracted with methylene chloride. Concentration of the organic layer provided 34 grams of an orange colored oil (B).

HPLC analysis of solid (A) gave a yield of felodipine of 0.0463% with a purity of 0.345 weight % pure. The majority of the isolated material in solid (A) was dichlorobenzylidine IIb of 99.12% weight purity. Dimethyl and diethyldihydropyridinediester impurities were not detected nor was the felodipine pyridine analog detected.

HPLC analysis of the oil (B) showed that the oil contained 30.7 weight % of felodipine (27.5% yield). The oil also contained 3.2 weight % of the starting dichlorobenzylidine IIb, 5.99 weight % of the dimethyldiester analog IIc, and 2.68 weight % of the diethyldiester analog IId. No aromatic pyridine analog was detected.

EXAMPLE 7

Preparation of Felodipine Involving Thermal Cyclization to Completion

A mixture of 27 g of dichlorobenzylidine IIb (98.6 mmol) and 15.7 g (121.2 mmol) of ethyl 3-aminocrotonate was dissolved in 25 mL ethanol. The reaction mixture was rapidly heated to 87° C. and stirred at 84° C. for 12.5 hours. The reaction temperature was then allowed to cool to room temperature and maintained at that temperature over the weekend. The mixture was then cooled to −15° C. and 30 mL of a 7:5 v/v water:ethanol solution was added dropwise. The mixture was then stirred an additional 30 minutes at −15° C. and the solid was then filtered. The solid was washed with 100 mL of a 1:1, ethanol:water solution (precooled to −10° to −15° C.). The solids were then dried under high vacuum at 40° C. until the weight remained constant to provide 33.3 g of the desired product I (HPLC 96.0% pure). 84.3% yield. Diethyl ester impurity 1.83 wt. % by HPLC.

What is claimed is:

1. A process for the preparation of a compound having the formula I:

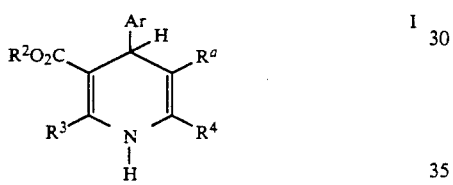

wherein

Ar is selected from:

a) 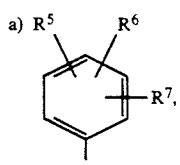

b) 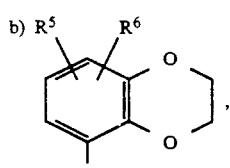

c) 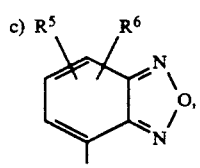

d) 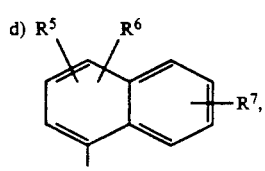

e) 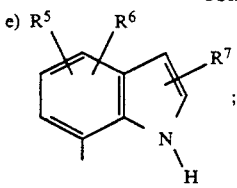

$R^a$ is selected from:

a) $\overset{O}{\underset{}{\overset{\|}{C}}}OR^1$, b) $\overset{X}{\underset{}{\overset{\|}{C}}}NR^8R^9$, and c) CN;

$R^1$ and $R^2$ are independently selected from:
  a) $C_1$-$C_8$-alkyl,
  b) $C_3$-$C_8$-cycloalkyl,
  c) $C_2$-$C_5$-alkenyl,
  d) $C_1$-$C_4$-aralkyl,
  e) $C_2$-$C_4$-aralkenyl
  f) -$C_1$-$C_5$-alkylNR$^8$R$^9$,
  g) -$C_1$-$C_4$-alkyl-O-$C_1$-$C_4$-alkyl,
  h) -$C_1$-$C_4$-alkylONO$_2$, i) 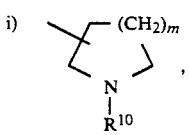

j) 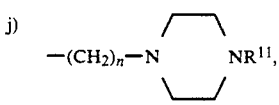

k) 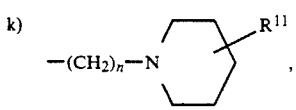

l) 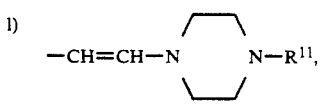

m) 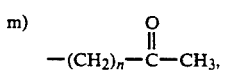

n) 

o) 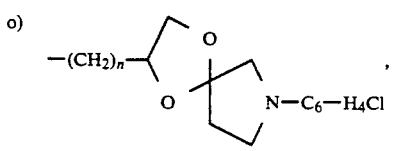

p) 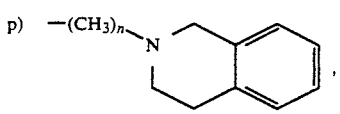

q) 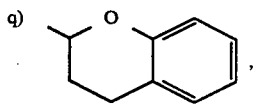

r) 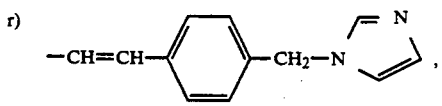

s) 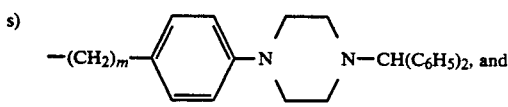

t) 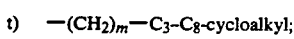

wherein $C_1-C_4$ aralkyl is selected from $C_1-C_4$-alkyl substituted one to two times with a group selected from phenyl and naphthyl;
wherein $C_2-C_4$ aralkenyl is selected from $C_2-C_4$-alkenyl substituted one to two times with a group selected from phenyl and naphthyl;
$R^3$ is selected from:
a) $C_1-C_8$-alkyl,
b) $C_3-C_8$-cycloalkyl,
c) $(CH_2)_n-R^{12}$, and
d) hydrogen;
$R^4$ is selected from:
a) $C_1-C_8$-alkyl,
b) $C_3-C_8$-cycloalkyl,
c) $(CH_2)_n-R^{12}$, and
d) hydrogen;
$R^5$, $R^6$, and $R^7$ are independently selected from:
a) hydrogen,
b) halogen,
c) $NO_2$, d) 

e) $CF_3$,
f) $C_1-C_8$-alkyl,
g) $C_3-C_8$-cycloalkyl,
h) ethynyl,
i) $-(CH_2)_n-R^{12}$, j) 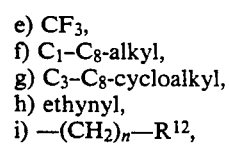, and k) $-O-(CH_2)_n-NH-CH_2-CH(OH)CH_2-O(C_6H_5)$;
$R^8$ and $R^9$ are independently selected from:
a) $C_1-C_8$-alkyl,
b) $C_3-C_8$-cycloalkyl,
c) aralkyl as defined herein above, and
d) hydrogen;
$R^{10}$ is selected from:
a) hydrogen,
b) $C_1-C_8$-alkyl,
c) $C_3-C_8$-cycloalkyl, and
d) $C_1-C_4$-aralkyl;
$R^{11}$ is selected from:
a) hydrogen,
b) $C_1-C_4$-aralkyl,
c) dichlorophenyl, and
d) $C_1-C_8$ alkyl, and
e) $C_3-C_8$-cycloalkyl;
$R^{12}$ is selected from:
a) halogen,
b) $NR^8R^9$,
c) $NHC(O)-C_1-C_8$-alkyl,
d) $SR^8$,
e) $SO_2$-pyridyl,
f) $OR^8$, and
g) $CO_2R^8$;
$R^{15}$ is selected from:
a) $-NR^8R^9$, and
b) -1-piperidinyl;
X is O, S, or $NR^8$;
m is 0 to 2; and
n is 0 to 3;
comprising the step of:
a) heating a mixture of a compound of the formula:

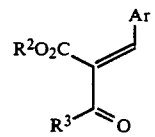    II wherein Ar, $R^2$, and $R^3$ are as defined hereinabove and a compound of the formula III:

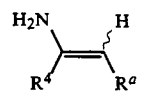    III wherein $R^a$ and $R^4$ are as defined hereinabove, in a solvent at an elevated temperature and for a length of time sufficiently long to consume the maximum amount of the starting materials but sufficiently short to allow only a minimum amount of the starting materials, intermediates or product to decompose
with a strong acid, wherein the strong acid is added subsequent to heating to the elevated temperature; to form the compound of the formula I.

2. The process according to claim 1 comprising the steps of:
a) heating a mixture of the compound of the formula:

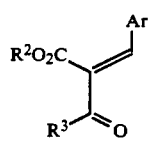    II wherein Ar, $R^2$, and $R^3$ are as defined hereinabove and the compound of the formula III:

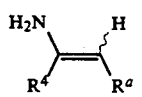    III wherein $R^a$ and $R^4$ are as defined hereinabove, in a solvent at an elevated temperature and for a length of time between 5 minutes and 10 hours; and
b) then adding a strong acid to the reaction mixture; to provide the compound of the formula I.

3. The process according to claim 2 wherein the solvent is a water miscible solvent.

4. The process according to claim 2 wherein the elevated temperature is between 65° C. and 130° C. and the length of time is between 30 minutes and 2 hours.

5. The process according to claim 2 wherein the elevated temperature and the length of time is a temperature and time sufficient to consume either or both of the compounds of formulas II and III.

6. The process according to claim 2 for the preparation of a compound selected from the group consisting of: amlopine, cronidipine, diperdipine, felodipine, furaldipine, lacidipine, manidipine, mepirodipine, nicardipine, nifedipine, nilvadipine, nimodipine, nisoldipine, nitrendipine, sagandipine and taludipine.

7. The process according to claim 2 which further comprises a step of:
c) heating the mixture with the acid present for an additional length of time at an elevated temperature.

8. The process according to claim 7 wherein the elevated temperature is between 65° C. and 130° C. and the additional length of time is between 10 minutes and 2 hours.

9. The process according to claim 2 for the preparation of a compound having the formula Ia:

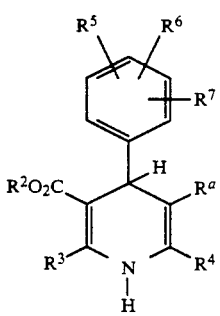

wherein
$R^a$ is selected from:

a) $\underset{COR^1}{\overset{O}{\parallel}}$, b) $\underset{CNR^8R^9}{\overset{O}{\parallel}}$, and c) CN;

$R^1$ and $R^2$ are independently selected from:
a) $C_1$-$C_8$-alkyl,
b) $C_3$-$C_8$-cycloalkyl,
c) $C_2$-$C_5$-alkenyl,
d) $C_1$-$C_4$-aralkyl,
e) $C_2$-$C_4$-aralkenyl
f) $-C_1$-$C_4$-alkyl-O-$C_1$-$C_4$-alkyl,
g) $-C_1$-$C_4$-alkyl-ONO$_2$, h) $-(CH_2)_n-\overset{O}{\overset{\parallel}{C}}-CH_3$, and i) 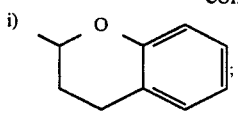

$R^3$ is selected from:
a) $CH_3$,
b) $CH_2F$,
c) CN, and
d) $CH_2$—$SO_2$-pyridyl;

$R^4$ is selected from:
a) $CH_3$,
b) $(CH_2)$—$NR^8R^9$, and
c) $(CH_2)_n$—$OR^{12}$, $R^5$, $R^6$, and $R^7$ are independently selected from:
a) hydrogen,
b) halogen,
c) $NO_2$, d) $-CH=CH-O-\overset{O}{\overset{\parallel}{C}}-t\text{-Bu}$, e) $C_1$-$C_8$-alkyl, and
f) $-O-(CH_2)_n-NH-CH_2CH(OH)C-H_2O(C_6H_5)$;

$R^8$ and $R^9$ are independently selected from:
a) $C_1$-$C_8$-alkyl,
b) $C_3$-$C_8$-cycloalkyl,
c) $C_1$-$C_4$-aralkyl, and
d) hydrogen;
m is 0 to 2; and
n is 0 to 3;
comprising the steps of:
a) heating a benzylidine of the formula IIa:

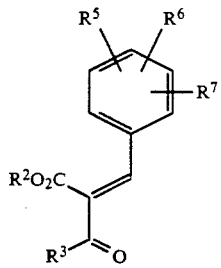

wherein $R^2$, $R^3$, $R^5$, $R^6$ and $R^7$ are as defined hereinabove and the compound of the formula III:

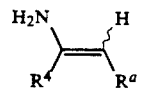

wherein $R^a$ and $R^4$ are as defined hereinabove, in a solvent at an elevated temperature and for a length of time between 5 minutes and 10 hours; and
b) then adding strong acid to the reaction mixture; to provide the compound of the formula Ia.

10. The process according to claim 9 wherein the solvent is a water miscible solvent.

11. The process according to claim 9 wherein the elevated temperature is between 65° C. and 130° C. and the length of time is between 30 minutes and 2 hours.

12. The process according to claim 9 wherein the elevated temperature and the length of time is a temperature and time sufficient to consume either or both of the compounds of formulas IIa and IIIA.

13. The process according to claim 9 for the preparation of a compound selected from the group consisting of: felodipine, lacidipine, nifedipine, nilvadipine, nimodipine, nisoldipine, and nitrendipine.

14. The process according to claim 2 for the preparation of a compound of the formula Ib, known as felodipine:

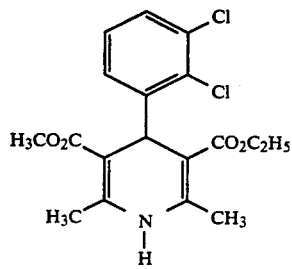

Ib comprising the steps of:
a) heating a mixture of a dichlorobenzylidine of the formula IIb:

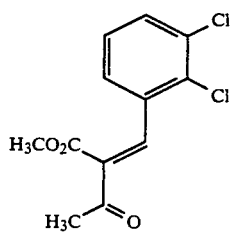

IIb and ethyl 3-aminocrotonate in a solvent at an elevated temperature between 50° and 140° C. and for a length of time between 30 minutes and 6 hours; and
b) then adding a strong acid to the reaction mixture; to provide felodipine.

15. The process according to claim 14 wherein the solvent is a low-molecular-weight alcohol.

16. The process according to claim 15 wherein the low-molecular-weight alcohol is selected from ethanol and isopropanol.

17. The process according to claim 14 wherein the reaction solution is heated at an elevated temperature and for a time sufficient to consume either or both of the compound of formula Ib and ethyl 3-aminocrotonate.

18. The process according to claim 14 wherein the strong acid is an aqueous acid solution or anhydrous methane sulfonic acid.

19. The process according to claim 18 wherein the aqueous acid solution is an aqueous hydrochloric acid solution in a low-molecular-weight alcohol.

20. The process according to claim 14 wherein the elevated temperature is between 65° C. and 100° C. and the length of time is between 30 minutes and 2 hours.

21. The process according to claim 20 wherein the elevated temperature is about 84° C. and the length of time is between 30 minutes and 1.5 hours.

22. The process according to claim 14 which further comprises the steps of:
c) cooling the solution to cause crystallization; and
d) collecting the crude felodipine by filtration.

23. The process according to claim 14 which further comprises a step of:
c) heating the mixture with the acid present for an additional length of time at an elevated temperature.

24. The process according of claim 23 wherein the elevated temperature is between 65° C. and 130° C. and the additional length of time is between 10 minutes and 2 hours.

* * * * *